(12) United States Patent
Ahn et al.

(10) Patent No.: US 8,894,893 B2
(45) Date of Patent: Nov. 25, 2014

(54) METHOD OF PREPARING SILICA AEROGEL GRANULES

(75) Inventors: Young-Soo Ahn, Daejeon (KR); Jeong-gu Yeo, Daejeon (KR); Churl-Hee Cho, Daejeon (KR)

(73) Assignee: Korea Institute of Energy Research, Daejeon (KR)

( * ) Notice: Subject to any disclaimer, the term of this patent is extended or adjusted under 35 U.S.C. 154(b) by 158 days.

(21) Appl. No.: 13/808,673

(22) PCT Filed: Sep. 28, 2011

(86) PCT No.: PCT/KR2011/007125
§ 371 (c)(1),
(2), (4) Date: Jan. 7, 2013

(87) PCT Pub. No.: WO2012/044052
PCT Pub. Date: Apr. 5, 2012

(65) Prior Publication Data
US 2013/0106008 A1  May 2, 2013

(30) Foreign Application Priority Data

Sep. 29, 2010  (KR) .................. 10-2010-0094775

(51) Int. Cl.
*C01B 33/158* (2006.01)
*B01J 2/08* (2006.01)
*C09K 3/00* (2006.01)

(52) U.S. Cl.
CPC ... *C07K 7/12* (2013.01); *B01J 2/08* (2013.01); *C01B 33/1585* (2013.01); *C09K 3/00* (2013.01)
USPC .................. 264/13; 264/5; 423/338

(58) Field of Classification Search
None
See application file for complete search history.

(56) References Cited

U.S. PATENT DOCUMENTS

| 5,391,364 | A  | * | 2/1995 | Cogliati ................. 423/335 |
| 6,197,270 | B1 | * | 3/2001 | Sonoda et al. ............. 423/338 |
| 6,451,862 | B1 | * | 9/2002 | Kusaka et al. ............. 516/111 |
| 2006/0084707 | A1 | * | 4/2006 | Ou et al. .................. 516/78 |
| 2008/0081014 | A1 | * | 4/2008 | Ahn et al. ................. 423/338 |
| 2010/0172815 | A1 | * | 7/2010 | Park et al. ................. 423/338 |
| 2012/0225003 | A1 | * | 9/2012 | Joung et al. ............... 423/338 |

FOREIGN PATENT DOCUMENTS

| KR | 100785521 B1 | 12/2007 |
| KR | 1020080047020 A | 5/2008 |
| KR | 1020090030132 A | 3/2009 |
| KR | 1020100010350 A | 2/2010 |

OTHER PUBLICATIONS

International Search Report dated Sep. 28, 2011 from International Application No. PCT/KR2011/007125.
Written Opinion dated Apr. 27, 2012 from International Application No. PCT/KR2011/007125.

* cited by examiner

*Primary Examiner* — Mary F Theisen
(74) *Attorney, Agent, or Firm* — Brian R. Morrison; Westman, Champlin & Koehler, P.A.

(57) ABSTRACT

A method of preparing transparent or nontransparent silica aerogel granules. The method includes forming a granular wet gel by spraying a silica sol into alcohol, the silica sol being prepared by mixing a water glass solution or an opacifier-containing water glass solution with an inorganic acid solution, forming a granular alcohol gel through gelation aging and solvent substitution of the granular wet gel in alcohol, hydrophobically modifying the surface of the granular alcohol gel using an organic silane compound, and drying the surface modified gel at ambient pressure or in a vacuum. The method may prepare silica aerogel granules in a short period of time through heat treatment at a relatively low temperature and at ambient pressure or in a vacuum, thereby ensuring excellent economic feasibility, continuity and reliability, suited for mass production.

8 Claims, No Drawings

METHOD OF PREPARING SILICA AEROGEL GRANULES

CROSS-REFERENCE TO RELATED APPLICATION(S)

This Application is a 371 National Stage Application of International Application No. PCT/KR2011/007125, filed on Sep. 28, 2011, published as International Publication No. WO2012/044052, which claims priority to Korean Patent Application No. 10-2010-0094775, filed on Sep. 29, 2010, the contents of which are incorporated by reference in their entireties.

TECHNICAL FIELD

The present invention relates to a method of preparing silica aerogel granules and, more particularly, to a method of preparing transparent or nontransparent silica aerogel granules, which employs ambient pressure drying process to prepare transparent or nontransparent silica aerogel granules in a short period of time at low cost.

BACKGROUND ART

Aerogels are super porous materials having a porosity of up to about 99% and a mesopore size of 50 nm or less, and exhibit lighter and better characteristics in terms of super heat-insulation/super lightness/super porosity/super low-dielectric properties than any other materials which have been developed to date. As a result, aerogels are spotlighted as fantastic materials which have broad applicability in energy/environment/electric and electronic fields as well as super heat-insulation materials. In particular, aerogels have a three-dimensional super porous network structure, pores of which have a smaller size than an average free path of air molecules. As a result, aerogels provide various merits, such as minimization of thermal conduction, avoidance of sound wave transfer, sunlight spreading, and hydrophobic properties, thereby enabling a wide range of applications in construction and other industries.

Aerogels have a thermal conductivity of about 0.025 W/m·K or less, which is much lower than any other known materials. As such, since silica aerogels exhibit such a low thermal conductivity, it has increasingly attracted attention towards application to LNG carriers, refrigerators, freezing machines, heat condensers, and the like. Silica aerogels are considered important materials not only in view of thermal conductivity but also in view of environment, since the silica aerogels exhibit superior heat insulating performance to polyurethane foam made of CFC causing destruction of the ozone layer or other toxic fibrous inorganic heat insulating materials.

Radiation heat transfer of aerogels is generally governed by absorption of infrared light. That is, at a low temperature of 20° C. or less, radiation heat transfer may easily occur by allowing infrared light at wavelength of 30 μm or more to be transmitted through the aerogel, and, at normal temperature and high temperature, the heat transfer may easily occur by allowing infrared light in the wavelength band of 2~8 μm to be transmitted through the aerogel. As a heat insulating material, the silica aerogel has a merit of visible light transparency, which allows the silica aerogel to be applied to windows or skylights. However, the aerogel also allows transmission of infrared light, particularly, in the wavelength band of 2~8 μm. Accordingly, although the aerogel does not cause any specific problem at low temperature due to low contribution of radiation heat transfer, it is necessary to minimize radiation heat transfer at high temperature in order to use the aerogel as a high temperature heat insulating material, since the radiation heat transfer is the main heat transfer mechanism of the aerogel at high temperature. As a method for reducing high temperature radiation heat transfer, opaque silica aerogel granules are prepared by adding an opacifier capable of absorbing infrared light at wavelengths of 8 μm or less to the silica aerogel.

Unlike silica aerogel granules, silica aerogel powder is prepared by placing an opacifier containing silica sol in a container or frame, followed by gelation and pulverization, thereby causing separation of the opacifier having a size of several micrometers or more from the silica gel. Further, even when the aerogel powder is directly prepared by adding an opacifier to a silica sol and is subjected to gelation, there is a problem of separation of the opacifier from the silica gel. Thus, the opacifier is not added in preparation of the silica aerogel powder. In addition, although the silica aerogel powder has thermal conductivity similar to that of the silica aerogel granules at room temperature, the silica aerogel powder has a particle size of about 10~20 μm and a very light weight, and is thus easily blown by wind, thereby causing difficulty in filling and handling of the powder. Moreover, the silica aerogel powder exhibits large heat radiation at high temperature, thereby limiting the applications range thereof.

In preparation of aerogel, it is an essential technique to dry the aerogel without contraction while maintaining a porous structure thereof. Generally, the overall process for aerogel preparation may be divided into a sol-gel process in which a gel is prepared from a sol, surface modification for hydrophobication in which the interior and surface of the gel are substituted by a solvent for modification, and a drying process. When evaporating the solvent in air during drying of the wet gel, the wet gel is likely to undergo contraction and cracking caused by differences in capillary force and solvent extraction rate at an air/liquid interface during the drying process, and a super-critical drying process is conventionally used to suppress such phenomena. However, supercritical drying is performed at high pressure and increases manufacturing costs, thereby providing an obstacle in commercialization of aerogels. Therefore, there is a need for development of a new ambient pressure drying process capable of solving problems of the supercritical drying process in terms of economic feasibility, safety, continuity, and the like. Further, in order to prepare silica aerogels at low cost, it is necessary to develop a process enabling continuous mass production of silica aerogels using inexpensive water glass and surface modifiers as starting materials instead of expensive alkoxide-based materials.

In the related art, when preparing silica aerogel granules using water glass, sodium components are generally removed from a water glass solution using an ion exchange resin to prepare a silica sol, which in turn is used to prepare granules. In addition, for gelation of the sol, a wet gel is produced by adding a basic substance to the silica sol and spraying liquid droplets of the silica sol into a non-polar organic solvent, or by dropping or spraying the silica sol into the non-polar organic solvent to which the basic substance has previously been added, followed by hydrophobication of the alcohol gel through surface modification and solvent substitution using an organic silane compound, and supercritical drying (U.S. Pat. No. 6,197,270). Further, as starting materials, expensive materials such as silicon alkoxide, alkyl silicate and alkoxy silane are used instead of water glass, and surface modification for hydrophobication and super-critical drying are sequentially performed (Japanese Patent Laid-open Publication No. H08-15120). As such, the silica aerogel granules are generally prepared using water glass, silicon alkoxide, and the like through supercritical drying.

Further, in ambient pressure drying, water glass is used as a starting material for cost reduction. The known process for preparing silica aerogel using water glass was very complicate and was not so productive and cost-effective because it is necessary to use cation exchange resins for removal of sodium ions from the water glass containing sodium components as impurities, a basic substance for inducing gelation through hydrolysis and polymerization, and various additives such as a dispersant for facilitating dispersion of silica gel in a non-polar organic solvent, a surface modifier, a substitution solvent, and the like in the separate steps.

DISCLOSURE

Technical Problem

The present invention is conceived to solve the problems of the related art, and the object of the present invention is to provide a method for rapid and continuous preparation of hydrophobic transparent or nontransparent silica aerogel granules at low cost without using an ion exchange resin and separate additives for granulation in ambient pressure drying using water glass.

Technical Solution

In accordance with one aspect of the invention, a method of preparing silica aerogel granules includes: forming a granular wet gel by spraying a silica sol into alcohol, the silica sol being prepared by mixing a water glass solution or an opacifier-containing water glass solution with an inorganic acid solution; forming a granular alcohol gel through gelation aging and solvent substitution of the granular wet gel in alcohol; hydrophobically modifying the surface of the granular alcohol gel using an organic silane compound; and drying the surface modified gel at ambient pressure or in a vacuum.

The inorganic acid solution may have a molar concentration of 1.0~2.0 M and may be mixed in a volume ratio of 0.4~1.0 with respect to the water glass solution. The alcohol may be used in a volume ratio of 0.6~1.2 with respect to the silica sol. If the molar concentration of the inorganic acid solution, the volume ratio of the inorganic acid solution, and the volume ratio of the silica sol are not within these ranges, a powder wet gel is formed instead of the granular wet gel when spraying the silica sol, or the gelation aging requires a long period of time.

Examples of the alcohol may include ethanol, isopropyl alcohol, and methanol, without being limited thereto.

The inorganic acid solution is prepared by diluting inorganic acid such as hydrochloric acid, sulfuric acid, or nitric acid hydrogen chloride in water to predetermined concentration. The inorganic acid may be at least one selected from the group consisting of hydrochloric acid, sulfuric acid, and nitric acid.

The opacifier may be at least one selected from the group consisting of carbon black, titania, alumina, iron oxide, and ilmenite.

The organic silane compound may be at least one selected from the group consisting of trimethylchlorosilane, hexamethyldisilazane, methyltrimethoxysilane, trimethylethoxysilane, ethyltriethoxysilane, and phenyltriethoxysilane.

In the hydrophobic surface modification, the organic silane compound may be mixed in a volume ratio of 2~5 with respect to the alcohol gel. If the volume ratio of the organic silane compound is less than 2, surface modification reaction time is excessively long, thereby making it difficult to obtain complete surface modification in a short period of time. On the other hand, if the volume ratio of the organic silane compound exceeds 5, rapid surface modification occurs, thereby causing surface cracking.

The surface modified gel may be dried at ambient pressure or in a vacuum. Preferably, drying the surface modified gel includes primary drying at a temperature of 50~90° C. for 1~2 hours and secondary drying at a temperature of 190° C. or less for 2~3 hours at ambient pressure or in a vacuum. More preferably, the surface modified gel is dried at 70° C. for 1 hour in a vacuum, followed by drying at 150° C. for 2 hours in a vacuum.

The silica aerogel granules prepared by the method may have a particle size of about 1 mm, a volume density of 0.056~0.101 g/Ml, a pore size of 9.3~17.2 nm, a pore volume of 2.4~4.0 Ml/g, a specific surface area of 705.9~825.3 $m^2$/g, and a low thermal conductivity of 0.019~0.023 W/m·K.

In the silica aerogel granules prepared by the method, aerogel powders are agglomerated to form granules having a particle size of about 1 mm, thereby facilitating filling and handling of the granules as compared with silica aerogel powder. The prepared silica aerogel granules may have any shape. For example, the prepared silica aerogel granules may have a spherical bid shape.

Transparent silica aerogel granules prepared by the method according to the invention without adding an opacifier may be readily used for skylights or double pane windows. Further, by adding an opacifier to the silica aerogel granules prepared by the method according to the invention, the silica aerogel granules do not allow radiation heat transfer at high temperature and thus may be applied to heat insulating panels or high temperature heat insulating components.

Next, the present invention will be described in more detail.

The method of preparing silica aerogel granules according to this invention includes the following steps.

First Step: Preparation and Spraying of Silica Sol to Form Granular Wet Gel

To prepare transparent silica aerogel granules, a water glass solution may be prepared without removing sodium components from water glass, and to prepare nontransparent silica aerogel granules, a water glass solution may be prepared by adding an opacifier in an amount of 5~20 wt % based on the total weight of silica in the water glass solution. A granular wet gel is formed as soon as a silica sol prepared by mixing the water glass solution and an inorganic acid solution is sprayed into alcohol.

The inorganic acid solution may have a molar concentration of 1.0~2.0 M and may be mixed in a volume ratio of 0.4~1.0 with respect to each of the water glass solutions when preparing the silica sol. Examples of the inorganic acid solution include hydrochloric acid, sulfuric acid, and nitric acid. Examples of the opacifier include carbon black, titania, alumina, iron oxide, ilmenite, or other oxides.

The alcohol is used in a volume ratio of 0.6~1.2 with respect to the volume of the silica sol. If the molar concentration of the inorganic acid solution, the volume ratio of the inorganic acid solution, and the volume ratio of the silica sol are not in the ranges described above, a powder wet gel is formed instead of the granular wet gel when spraying the silica, or a wet gel is not formed. The silica aerogel granules may be prepared by adjusting the concentration of an acid solution in the silica sol, the volume ratio of the water glass solution to the inorganic acid solution, and the amount and kind of alcohol. Examples of the alcohol include ethanol, isopropyl alcohol, and methanol, without being limited thereto.

The silica sol for the silica aerogel granules may be prepared by adjusting process conditions, such as the molar concentration of the inorganic acid solution, the mixing ratio of the inorganic acid solution with respect to the silica sol, and the like.

Second Step: Gelation Aging/Solvent Substitution

The prepared granular wet gel is subjected to gelation aging in alcohol and the like acting as a gelation catalyst and a substitution solvent, and left for a predetermined period of time to substitute water in the wet gel by the alcohol and the like, thereby preparing an alcohol gel.

In the related art, a silica sol, from which sodium components have been removed, is supplied dropwise or sprayed into a non-polar organic solvent containing a basic substance, a dispersant, and the like, and is subjected to hydrolysis and polymerization for gelation to form a wet gel, followed by substitution using an non-polar organic solvent. On the contrary, according to the invention, gelation aging and solvent substitution can be performed at the same time by spraying the silica sol into alcohol which acts as the gelation catalyst and the substitution solvent and obtaining alcohol gel, thus such processes, i.e, hydrolysis and polymerization for gelation in the related art can be omitted.

Third Step: Hydrophobic Surface Modification

The alcohol gel obtained in the second step is subjected to surface modification for hydrophobication of the alcohol gel using an organic silane compound. Examples of the organic silane compound may include trimethylchlorosilane (TMCS), hex amethyldisilazane (HMDS), methyltrimethoxysilane, trimethylethoxysilane, ethyltriethoxysilane, and phenyltriethoxysilane.

In hydrophobic surface modification, the organic silane compound may be mixed in a volume ratio of 2~5 with respect to the alcohol gel. If the volume ratio of the organic silane compound is less than 2, surface modification reaction time is excessively long, thereby making it difficult to obtain complete surface modification of the alcohol gel in a short period of time. On the other hand, if the volume ratio of the organic silane compound exceeds 5, rapid surface modification occurs, thereby causing surface cracking.

Fourth Step: Drying

The surface modified alcohol gel is subjected to two-stage drying at a temperature of 50~190° C. for 1~4 hours at ambient pressure or in a vacuum. Preferably, drying the surface modified gel includes primary drying at a temperature of 50~90° C. for 1~2 hours in a vacuum and secondary drying at a temperature of 190° C. or less for 2~3 hours in a vacuum. More preferably, drying the surface modified gel includes primary drying at a temperature of 70° C. for 1 hour in a vacuum and secondary drying at a temperature of 150° C. for 2 hours in a vacuum. In this case, it is possible to prevent cracking which can occur during drying of the granular alcohol gel subjected to the hydrophobic surface modification.

Advantageous Effects

In the method of preparing silica aerogel granules according to the present invention, a silica sol is supplied dropwise or sprayed into alcohol acting as a gelation catalyst and a substitution solvent through a spray nozzle or the like to prepare a granular wet gel, which in turn is subjected to gelation aging while being left for a predetermined period of time to achieve solvent substitution of water of the wet gel by alcohol to prepare an alcohol gel, followed by hydrophobic surface modification of the alcohol gel, and heat treatment at a relatively low temperature at ambient pressure or in a vacuum, so that the silica aerogel granules can be prepared in a short period of time, thereby ensuring excellent economic feasibility, continuity and reliability, suited for mass production.

Further, silica aerogel granules prepared by the method according to the present invention are easier to fill and handle than silica aerogel powder.

BEST MODE

The following examples are provided to assist in a further understanding of the invention. However, these examples are intended for illustrative purposes only and those skilled in the art will appreciate that various modifications and changes are possible without departing from the spirit and scope of the invention. It should be understood that such modifications and changes are within the scope of the appended claims.

Example 1

425 Ml of water was added to 75 Ml of commercially available water glass (3-ho, 29.0 wt % of $SiO_2$, Young-il Chemical Co., Ltd) to prepare a water glass solution containing 4.35 wt % of $SiO_2$, and 80 Ml of the water glass solution was used for a subsequent process. For transparent silica aerogel granules, diluted water glass without opacifier were used.

40 Ml of 1.1 M nitric acid solution corresponding to ½ of the water glass in terms of volume was mixed with the water glass, followed by stirring for 3~5 minutes, thereby preparing 120 Ml of a silica sol. 60 Ml of methanol was prepared corresponding to ½ of the silica sol in terms of volume. A granular wet gel was formed by spraying 120 Ml of the silica sol into 60 Ml of methanol using nozzle spray, and left for 1 hour in methanol for gelation aging and solvent substitution by which water in the wet gel was substituted by methanol, thereby preparing an alcohol gel. The overall process for preparing the alcohol gel from the water glass was performed within 60 minutes.

As a solvent for modification of the surface of the alcohol gel into a hydrophobic surface, trimethylchlorosilane was used. Here, the alcohol gel was placed in a container filled with trimethylchlorosilane for hydrophobic surface modification at room temperature for 4 hours. The surface modified granular alcohol gel was then subjected to drying at 70° C. for 1 hour and drying at 150° C. for 2 hours at ambient pressure using a drier, thereby preparing silica aerogel granules.

The prepared silica aerogel granules have a density of 0.068 g/Ml, a specific surface area of 809.3 $m^2$/g, an average pore size of 11 nm, and a pore volume of 3.68 Ml/g.

Examples 2 and 3

Preparation of Silica Aerogel Granules According to Molar Concentration of Nitric Acid Example 2

Silica aerogel granules according to Example 2 were obtained by the same process as in Example 1 except that 60 Ml of 1.2 M nitric acid solution was used.

Example 3

Silica aerogel granules according to Example 3 were obtained by the same process as in Example 1 except that 60 Ml of 1.5 M nitric acid solution was used.

As can be seen from the following Table 1, the silica aerogel granules increased in volume density from 0.068 g/Ml to 0.092 g/Ml, and decreased in, specific surface area, and size and volume of fine pores, with increasing molar concentration of the nitric acid in Examples 1 to 3.

Examples 4 and 5

Preparation of Silica Aerogel Granules According to Addition of Opacifier

Example 4

Nontransparent silica aerogel granules according to Example 4 were obtained by the same process as in Example 1 except that titania was added to diluted water glass in an amount of 5.0 wt % based on the weight of silica in the water glass.

Example 5

Nontransparent silica aerogel granules according to Example 5 were obtained by the same process as in Example 1 except that carbon black was added to diluted water glass in an amount of 5.0 wt % based on the weight of silica in the water glass.

When titania was added as the opacifier as in Examples 4 and 5, the silica aerogel granules increased in volume density and decreased in pore volume and specific surface, as compared with Examples 1 to 3 where no opacifier was added. Further, the silica aerogel granules increased in volume density, and particularly, significantly decreased in pore volume, when the carbon black was added as the opacifier.

Examples 6 and 7

Preparation of Silica Aerogel Granules According to the Kind of Alcohol

Example 6

Silica aerogel granules according to Example 6 was obtained by the same process as in Example 1 except that 60 Me of ethanol was used instead of methanol.

Example 7

Silica aerogel granules according to Example 6 was obtained by the same process as in Example 1 except that except that 60 Ml of isopropyl alcohol was used instead of methanol.

When ethanol or isopropyl alcohol was used instead of methanol as in Examples 6 and 7, the silica aerogel granules increased in volume density and slightly decreased in specific surface area, size and volume of pores as compared with Example 1.

Example 8

Silica aerogel granules according to Example 8 was obtained by the same process as in Example 1 except that drying was performed at 70° C. for 1 hour in a vacuum and then at 150° C. for 2 hours in a vacuum.

When drying was performed in a vacuum as in Example 8, the physical properties of the silica aerogel granules were improved as compared with Examples 1 to 7 where drying was performed at ambient pressure.

Volume density, size and volume of pores and thermal conductivity of the silica aerogel granules prepared in Examples 1 to 8 are listed in Table 1.

TABLE 1

| No. | Volume density [g/Mℓ] | BET area [m$^2$/g] | Pore size [nm] | Pore volume [Mℓ/g] | Thermal conductivity [W/m · K] |
| --- | --- | --- | --- | --- | --- |
| Example 1 | 0.068 | 809.3 | 11.0 | 3.68 | 0.020 |
| Example 2 | 0.084 | 732.5 | 10.2 | 2.99 | 0.022 |
| Example 3 | 0.092 | 720.7 | 9.9 | 3.07 | 0.022 |
| Example 4 | 0.098 | 719.4 | 9.5 | 2.87 | 0.022 |
| Example 5 | 0.101 | 705.9 | 9.3 | 2.41 | 0.023 |
| Example 6 | 0.072 | 793.2 | 10.5 | 3.43 | 0.021 |
| Example 7 | 0.076 | 778.6 | 10.1 | 3.32 | 0.021 |
| Example 8 | 0.056 | 825.3 | 17.2 | 3.97 | 0.019 |

The invention claimed is:

1. A method of preparing silica aerogel granules, comprising:
    forming a granular wet gel by spraying a silica sol into alcohol, the silica sol being prepared by mixing a water glass solution or an opacifier-containing water glass solution with an inorganic acid solution;
    forming a granular alcohol gel through gelation aging and solvent substitution of the granular wet gel in alcohol;
    hydrophobically modifying a surface of the granular alcohol gel using an organic silane compound; and
    drying the surface modified gel at ambient pressure or in a vacuum.

2. The method of claim 1, wherein the inorganic acid solution has a molar concentration of 1.0~2.0M and is mixed in a volume ratio of 0.4~1.0 with respect to the water glass solution, and the alcohol is used in a volume ratio of 0.6~1.2 with respect to the silica sol.

3. The method of claim 1, wherein the inorganic acid is at least one selected from the group consisting of hydrochloric acid, sulfuric acid, and nitric acid.

4. The method of claim 1, wherein the opacifier is at least one selected from the group consisting of carbon black, titania, alumina, iron oxide, and ilmenite.

5. The method of claim 1, wherein the alcohol is at least one selected from the group consisting of ethanol, methanol, and isopropyl alcohol.

6. The method of claim 1, wherein the organic silane compound is at least one selected from the group consisting of trimethylchlorosilane, hexamethyldisilazane, methyltrimethoxysilane, trimethylethoxysilane, ethyltriethoxysilane, and phenyltriethoxysilane.

7. The method of claim 1, wherein the organic silane compound is mixed in a volume ratio of 2~5 with respect to the granular alcohol gel when hydrophobically modifying the surface of the granular alcohol gel.

8. The method of claim 1, wherein the drying of the surface modified gel is performed at a temperature of 50~90° C. for 1~2 hours and then at a temperature from a solvent boiling point to 190° C. for 2~3 hours at ambient pressure or in a vacuum.

* * * * *